US005352443A

United States Patent [19]
Kubo et al.

[11] Patent Number: 5,352,443
[45] Date of Patent: Oct. 4, 1994

[54] PERMANENT WAVING COMPOSITION

[75] Inventors: Sanae Kubo, Darien; Thomas M. Schultz, Ridgefield, both of Conn.

[73] Assignee: Shiseido Co., Ltd., Tokyo, Japan

[21] Appl. No.: 67,346

[22] Filed: May 25, 1993

Related U.S. Application Data

[63] Continuation of Ser. No. 898,420, Jun. 15, 1992, abandoned.

[51] Int. Cl.$^5$ .......................... A61K 7/09; A61K 7/11
[52] U.S. Cl. ........................................ 424/72; 424/71; 132/203
[58] Field of Search ................................... 424/71, 72

[56] References Cited

U.S. PATENT DOCUMENTS

| | | | |
|---|---|---|---|
| 3,578,686 | 5/1971 | Tullar | 260/396 R |
| 3,993,436 | 11/1976 | Fujinama | 8/10.2 |
| 4,096,190 | 6/1978 | Rutledge | 568/730 |
| 4,187,251 | 2/1980 | Schleppnik | 424/76.2 |
| 4,548,811 | 10/1985 | Kubo | 424/71 |
| 4,560,554 | 12/1985 | Kubo | 424/71 |
| 5,006,331 | 4/1991 | Gaskin | 424/70 |

*Primary Examiner*—Thurman K. Page
*Assistant Examiner*—Sally Gardner
*Attorney, Agent, or Firm*—Melvin I. Stoltz

[57] ABSTRACT

An improved permanent waving lotion is attained by incorporating into an otherwise conventional composition an organic compound having at least one function position definable as an alpha, beta-unsaturated ketone in conjunction with a carbon-carbon double bond. By employing the present invention, improved curl formation is attained and the malodor typically associated with permanently waved hair is substantially eliminated. Compounds incorporating the desired alpha, beta-unsaturated ketone can be used directly, in the permanent waving lotion, or chemical precursors can be employed to produce the desired alpha, beta-unsaturated ketone when exposed to oxidation or to alkaline materials.

10 Claims, No Drawings

PERMANENT WAVING COMPOSITION

This application is a continuation, of application Ser. No. 07/898,420, filed Jun. 15, 1992, now abandoned.

TECHNICAL FIELD

This invention relates to the art of permanent waving of hair, and more particularly to novel additives or compositions therefor which impart substantially improved curl characteristics to the hair while also virtually eliminating the objectionable order typically associated with permanent waving.

BACKGROUND ART

The common practice in the art of permanent waving involves the reformation of hair about a mold to impart long wearing control in the new shape. This action is obtained by first placing the hair under tension, such as by wrapping the hair about a form. The most common form is a rod shaped device which serves as a template for the "curls" desired.

Once the hair has been placed about the mold, it is then treated with certain aqueous solutions of chemicals which allow for the internal structure of the hair fiber system to enter into a plasma state. While in this plasma state, the fibers within the hairs central portion, known as the cortex, acquire this new shape.

The chemicals typically employed in this action are of the chemical class of mercaptans, that is organic compounds which have terminal atoms of sulfur. In such permanent wave compositions, the lotions typically comprise aqueous solutions of sulfur-oxygen compounds such as bisulfite, sulfite, and the like. It is also common to employ the use of alkali salts of these latter materials to case the formulation of such lotions.

Once the hair has been saturated with the waving lotion and has been molded about the rod, it is left to stand for a prescribed amount of time. This allows for the maximum amount of fiber repositioning to occur. The net effect of application of an aqueous lotion of mercaptan to hair is the chemical alteration of its interior molecular structure. While there is uncertainty as to the actual composition of hair, it is established that much of the internal binding forces of hair is due to the presence of disulfide bonds which crosslink the proteinaceous areas of the cortex. This can be stylized by the representation of:

K—S—S—K where K is the keratin structure of hair and S—S is the disulfide cross-link.

In permanent waving, the mercaptan reacts with the keratin disulfide to generate two equivalents of keratin sulfide:

K—S—S—K+2RSH  2K—SH—+R—S—S—R where RSH is mercaptan. The keratin sulfide is then forced to undergo annealation by the addition of an oxidizing agent to the hair. This reforms the cortex inner structure in its new state. It is known that depending on the ability to remove residual mercaptan and K—S—S—R, known as a mixed disulfide, the hair will have a maleder.

Although substantial effort that has occurred in prior art permanent wave compositions, these prior art compositions have been incapable of eliminating or substantially reducing the maleder resulting from the permanent wave procedure. Although various prior art attempts have been made, no successful or elimination or substantial reduction of this maleder has been attained.

An additional problem found in prior art permanent wave formulations is the continuing desire to attain a tighter permanently waved curl as a result of the permanent wave application. In spite of substantial efforts to improve curl tightness in the prior art compositions, there has been a general inability to provide the degree of curl tightness sought by the consuming public.

Furthermore, the industry has also sought to increase the luster, sheen, gloss and manageability of the hair as well as provide a permanently waved head of hair which is soft, supple, and possesses a natural feel. However, these goals have not been fully attained.

Therefore, it is a principal object of the present invention to provide a cold permanent waving formulation which virtually eliminates the malodor typically associated with permanent waving procedures.

Another object of the present invention is to provide a cold permanent waving formulation having the characteristic features described above which also provides a substantially tighter curl configuration than previously attainable.

Another object of the present invention is to provide a cold permanent waving formulation having the characteristic features described above which also imparts to the permanently waved head of hair a high luster, gloss, sheen and improved manageability.

A further object of the present invention is to provide a cold permanent waving formulation having the characteristic features described above which also imparts to the permanently waved head of hair a full bodied appearance which is easily managed.

Other and more specific objects will in part be obvious and will in part appear hereinafter.

DETAILED DESCRIPTION OF THE INVENTION

By employing the present invention, the prior art inabilities and drawbacks have been substantially eliminated and an improved curl configuration is obtained, while the malodor is virtually eliminated. These previously unobtainable goals are realized in the present invention by incorporating into the waving lotion specific quantities of organic compounds having at least one functional position with the common structural entity of an alpha, beta-unsaturated ketone contained within a conjugated pi electron network. The basic structure of these compounds is described by structure A. However, in the preferred embodiment, the alpha, beta-unsaturated ketone comprises a cyclic organic compound.

$$\begin{array}{c} O \\ \parallel \\ C \\ / \quad \backslash \\ R \quad\quad CH \\ \phantom{R}\quad \parallel \\ \phantom{R}\quad C \\ / \quad \backslash \\ R' \quad R'' \end{array} \quad \text{Structure A}$$

wherein R, R', R''=H, CH$_3$, CH$_2$—, aryl, cyclic aliphatics, and members of cyclic aliphatics.

As is fully detailed herein, the alpha, beta-unsaturated ketones employed in the present invention preferably comprise at least one functional position of the organic compound being employed with the alpha, beta-unsaturated ketone being in conjunction with a carbon-carbon double bond. In Table I, a representative list of chemical species and structures employable in the present invention are provided. As detailed in Table I, as well as below, some of these chemicals comprise alpha, beta-unsaturated ketones as defined by Structure A, while other chemicals defined in Table I as precursors must be oxidized or exposed to an alkaline solution in order to form the alpha, beta-unsaturated ketone.

TABLE I

| STRUCTURE | NAME | ABBREV. |
|---|---|---|
| Alpha, Beta-Unsaturated Ketones | | |
| [structure] | D&C Yellow No. 8 | Yel-8 |
| [structure] | Lawsone | LAW |
| Unknown | Melanin (sepia officianalis) | SEP |
| Unknown | Pheomelanin (condensate of CysHQ) | Pheo |
| [structure] | Hematin | HEMA |
| Precursors | | |
| [structure] | Catechol | CAT |
| [structure] | 3,4-Dihydroxy-phenylalanine | DOPA |
| [structure] | 4-Hydroxyindole | 4-HI |
| [structure] | 5-Hydroxyindole | 5-HI |
| [structure] | 2-S-Cysteinyl-1,4-hydroquinone | CysHQ |

TABLE I-continued

| STRUCTURE | NAME | ABBREV. |
|---|---|---|
| | 3'-Hydroxy-2,2,3,3-tetra-hydrophenothaizine | PhenOH |
| 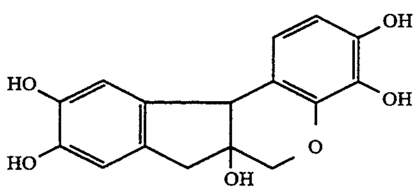 | Hematoxylin | HEM |
| 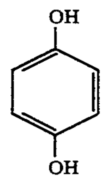 | Hydroquinone | HQ |
| 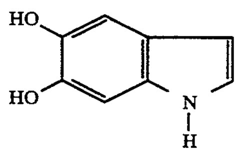 | 5,6-Dihydroxyindole | DI |
| 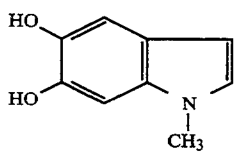 | N-Methyl-5,6-dihydroxyindole | NMDI |

This list of chemicals detailed in Table I is not intended to be all-inclusive, since numerous other, unstated compounds are in existence and come within the scope of this invention. However, Table I is presented as a showing of representative chemical species which produce the desired alpha,beta-unsaturated ketone upon oxidation, or comprise the desired alpha, beta-unsaturated ketone in their present form.

Included in Table I are several materials of natural origin as well as several materials produced under controlled organic synthetic routes to provide end synthetic products which resemble the natural products. Specifically, materials such as hematin (Merck Index) Bloodroot Extract is derived from animal and plant sources.

Furthermore, the oxidation of phenothiazine and hydroxyindoles produce the classes of mammalian pigments known as melanins, specifically the reddish-brown pheomelanin and black eumelanins respectively. While these latter materials in their natural proteinaceous form, as isolated from mammalian sources, tend to be quite insoluble in water, it has been found that in the low concentrations described in this application, they tend to become soluble, or at least stable dispersions, and perform quite satisfactorily in this discovery.

The melanins are reputed to contain certain amounts of the alpha,beta-unsaturated ketone organic functional groups in conjugation with extended delocalized electronic configurations. Such structure is consistent with the effect of lowering perm malodor as observed with the pure coloring agents also discovered to be operative.

The present invention is exemplified by the discovery that specific quantities of organic compounds which have at least one functional position of the description of an alpha,beta-unsaturated ketone in conjunction with a carbon-carbon double bond, as defined in structure A, is able to virtually eliminate the malodor associated with permanent waving, as well as impart an improved permanent wave to the head of hair. Preferably, the alpha,beta-unsaturated ketone comprise a concentration of between about 0.001 to 0.1% by weight in admixture with a hydroxylated ester of an organic acid of sulfur. Preferably, the hydroxylated ester of the organic salt of sulfur comprises a concentration of between about 10% to 20% by weight. By employing this formulation, an excellent permanent wave is attained with very little to no malodor being sensed.

An additional discovery which has been found as part of this invention is that the amount of thioglycolate ester required may be reduced by as much as 35% by weight when the composition of this invention is employed. It has been found that by employing the waving lotion of this invention with a substantially reduced quantity of thioglycolate, the resulting permanently waved hair possessed curls equivalent to compositions with the normal amount of thioglycolate, but containing no alpha, beta-unsaturated ketone.

The actual mechanism by which the process of this invention operates is unknown and it is not the intention of this disclosure to suggest any such process. However, it has been found that one specific component associated with the malodor of permanent waving of human hair, namely hydrogen sulfide, $H_2S$, is decreased significantly in the reactions resulting from the present invention. It has been found that in some instances the hydrogen sulfide concentrations are reduced by as much as a factor of 75 to 100.

Although not mandatory, it is preferred that the present invention is carried out using wave lotion composed of two parts. One part comprises an alkaline solution which contains the alpha, beta-unsaturated ketone. The alkaline solution also preferably comprises a mixture of de-ionized water and an alkalizing agent sufficient to bring the pH of the solution to an alkaline pH, typically around 9. In addition, the alkalizing agent employed should also be able to maintain the pH of the intermixed composite waving lotion at a pH ranging between about 7 and 7.8.

The second part of the waving lotion is the additive solution and comprises an ester of thioglycolic acid in a composition with glycerine and having a concentration in the range of between about 11% and 25% by weight. When mixed with the alkaline component to form the intermixed permanent waving lotion, the total active concentration of this ester of thioglycolic acid ranges between about 7% and 18% by weight. In this invention, it has been found that the ester may comprise a functional group consisting of aliphatic, a hydroxyaliphatic, aryl, alkoxylamine, and the like.

BEST MODE FOR CARRYING OUT THE INVENTION

In order to clearly and precisely define the unique, novel, and unobvious compositions and methods that have been developed by the present invention for permanently waving hair, while attaining the substantial improvements detailed above, the following examples are presented to teach the best mode for carrying out this invention. In addition, these examples substantiate the discovery that has been made and the advance that has been achieved by the present invention over the prior art.

In the following examples, separate and distinct detailed formulations are provided, each of which were made and tested in order to determine their efficacy as well as the efficacy of the present invention. In most of the examples, the waving lotion comprised a two-part solution, the parts of which were intermixed immediately prior to application to the hair. In addition, for purposes of clarity and completeness, the formulations employed for the neutralizer are also provided in each example. Finally, pre and post hair treatment in each example was identical with the actual application of the waving lotion and the neutralizer being performed in the conventional manner.

EXAMPLE 1

In Example 1, D&C Yellow No. 8 and hematin were employed as the alpha, beta-unsaturated ketone of the present invention in the waving lotion. The precise formulation for this waving lotion and neutralizer were as follows:

| WAVING LOTION | Part I | GMTG (80%) | 20.0 g |
|---|---|---|---|
| | Part II | Ammonium Chloride | 2.0 g |
| | | Urea | 4.0 g |

-continued

| | | |
|---|---|---|
| | D&C Yellow No. 8 | 0.001 g |
| | Hematin | 0.003 g |
| | Ammonium Hydroxide (28%) | Adjust part I, II mixed pH is 8.0 |
| | Hydrolized Silk Protein | 0.5 g |
| | DC 929 | 3.0 g |
| | Laureth 23 | 0.5 g |
| | Fragrance | 0.2 g |
| | Deionized Water | qs to 80.0 g |
| NEUTRALIZER | Hydrogen Peroxide (30%) | 7.7 g |
| | Phosphates | Adjust pH to 4.0 |
| | Deionized Water | qs to 100.0 g |

EXAMPLE 2

In Example 2, the alpha, beta-unsaturated ketone comprised 2-S-cysteinyl-1,4-hydroxyquinone which was obtained by creating an aqueous solution consisting of 0.5% by weight of CysHQ and 0.25% NaOH, and allowing these ingredients to react for one hour prior to mixing part one and part two of the waving lotion. The precise formulation for both the waving lotion and the neutralizer in this example were as follows:

| WAVING LOTION | Part I | GMTG (80%) | 20.0 g |
|---|---|---|---|
| | Part II | Ammonium Sulfonate | 1.8 g |
| | | 1,3-Butyleneglycol | 3.0 g |
| | | Oxidized CysHQ 0.5% soln. | 5.0 g |
| | | Ammonium Hydroxide (28%) | Adjust Part I, II mixed pH to 7.0 |
| | | Cocobetain (30%) | 1.0 g |
| | | Laureth-25 | 0.5 g |
| | | Fragrance | 0.2 g |
| | | Deionized Water | qs to 80.0 g |
| NEUTRALIZER | | Hydrogen Peroxide (30%) | 5.5 g |
| | | Phosphates | Adjust pH to 4.0 |
| | | Deionized Water | qs to 100.0 g |

EXAMPLE 3

In Example 3, the alpha, beta-unsaturated ketone comprised 3-hydroxy-2-carboxy-phenothiazine. This alpha, beta-unsaturated ketone was obtained by oxidizing CysHQ. Oxidized CysHQ was generated by aerating a 0.5% solution of CysHQ having a pH of 10 for twenty-four hours prior to preparing the waving lotion. The formulation for the waving lotion and neutralizer were as follows:

| WAVING LOTION | GMTG (80%) | 20.0 g |
|---|---|---|
| | Ammonium Citrate | 3.5 g |
| | Urea | 10.0 g |
| | Oxidized CysHQ 0.5% soln. | 0.4 g |
| | L-Arginine | 2.0 g |
| | Monoethanolamine | Adjust Part I, II mixed pH is 8.0 |
| | Deionized Water | qs to 80.0 g |
| NEUTRALIZER | Hydrogen Peroxide | 8.0 g |
| | Phosphates | Adjust pH to 4.0 |
| | Deionized Water | qs to 100.0 g |

EXAMPLE 4

In Example 4, 5,6-dihydroxyindole was employed as a precursor to attain synthetic eumelanin as the alpha, beta-unsaturated ketone. In this application, an aqueous solution was prepared comprising 0.5% of 5,6-dihydroxyindole along with 0.25% of KOH and aerating the aqueous solution for one hour prior to employing this solution in the waving lotion formulation. The precise formulation for both the waving lotion and the neutralizer were as follows:

| WAVING LOTION | Part I | GMTG (80%) | 20.0 g |
|---|---|---|---|
| | | Polyoxyethylene (5 E.O.) Dithioglycolate | 5.0 g |
| | Part II | Guanidine Carbonate | 3.0 g |
| | | Dimethyl Urea | 5.0 g |
| | | Oxidized 5,6-Dihydroxy Indole 0.5% soln. | 0.1 g |
| | | Monoethanolamine | Adjust Part I, II mixed pH to 7.5 |
| | | Hydrolized Soy Protein | 0.1 g |
| | | Oleth-20 | 0.5 g |
| | | Deionized Water | qs to 75.0 g |
| NEUTRALIZER | | Hydrogen Peroxide (30%) | 6.0 g |
| | | Phosphates | Adjust pH to 4.0 |
| | | Deionized Water | qs to 100.0 g |

EXAMPLE 5

In Example 5, a melanin solution was employed as the principal source of alpha, beta-unsaturated ketone for the permanent waving lotion. In obtaining this solution, 0.5% by weight of sepia officianalis melanin powder was mixed in an aqueous solution containing 0.25% by weight of NaOH. The aqueous solution was refluxed for one hour prior to completing the permanent waving lotion. The precise formulation for the waving lotion and the neutralizer were as follows:

| WAVING LOTION | Part I | GMTG (80%) | 20.0 g |
|---|---|---|---|
| | | Hematin | 0.001 g |
| | Part II | Ammonium Chloride | 1.0 g |
| | | Urea | 4.0 g |
| | | Melanin soln | 0.5 g |
| | | Ammonia (28%) | Adjust Part I, II mixed pH to 8.0 |
| | | Hydrolized Silk Protein | 0.1 g |
| | | Deionized Water | qs to 80.0 g |
| NEUTRALIZER | | Hydrogen Peroxide (30%) | 7.0 g |
| | | Phosphates | Adjust pH to 4.0 |
| | | Deionized Water | qs to 100.0 g |

EXAMPLE 6

In Example 6, an oxidized melanin substantially identical to the solution used in Example 5 was employed as the alpha, beta-unsaturated ketone, but incorporated into a waving lotion having a different composition. In this example, 0.5% by weight of sepia officianalis melanin powder was added to an aqueous solution along with 0.5% of NaOH. The aqueous solution was refluxed for one hour prior to inter-mixing the desired amount with the remaining components of the waving lotion. The precise formulation for the waving lotion is as follows:

| WAVING LOTION | Ammonium Thioglycolic Acid (60%) | 15.0 g |
|---|---|---|
| | Ammonium Hydroxide (28%) | 3.0 g |
| | Ammonium Bicarbonate | Adjust pH to 8.5 |
| | Melanin soln | 0.5 g |
| | Hematin | 0.005 g |
| | DCQ2-7224 | 1.0 |
| | Oleth 23 | 0.5 |
| | Fragrance | 0.1 |
| | 3Na—EDTA | 0.1 |
| | Deionized Water | qs to 100.0 g |
| NEUTRALIZER | Sodium Bromate | 8.0 |
| | Phosphates | Adjust pH to 6.5 |
| | Deionized Water | qs to 100.0 g |

Each of the permanent waving lotions detailed in Examples 1–6 were prepared and used in the normal manner to permanently wave a plurality of different heads of hair. Based upon the results obtained, it was found that each of the six alternate compositions were substantially equivalent in their efficacy, with each composition providing substantially equivalent permanent waving characteristics. In each instance, tighter curls were formed and virtually no malodor was sensed, when compared to conventional prior art permanent waving applications.

In order to employ the present invention most effectively, it was discovered that the use of the chemical precursors defined in Table I are best employed in an undisturbed form or as relatively pure materials, free from any chemical modification or at a minimum, in only a moderately changed state. It has been found that these precursor materials, such as 2-S-cysteinyl-1,4-hydroquinone (CysHQ), comprise disguised alpha, beta-unsaturated ketone. Upon activation of these chemicals by an oxidizing agent, or the action of an alkali, the phenolic version is transformed into its ketone state, thereby becoming activated. In this way, a substantially increased, enhanced, synergistic effect is realized, particularly when the chemical species of Table I are fully transformed into their completely oxidized state, with the alpha,beta-unsaturated ketone being fully developed by the action of an oxidizing material or an alkali agent.

In order to prove the efficacy of the present invention and quantitatively define the advantageous results realized by the present invention on the wave produced, the curl quality was determined by quantitative measurements, using a method termed the Test Tube Test Curl method (TITC). In this method, a predetermined quantity of human hair, in this case twelve strands of hair fibers, were knotted at the root end and trimmed to a length of 90mm from the knot. All of the hair fibers employed were virginal, namely hair fibers that had not been previously treated with any cosmetic process. In this way, damage that may be caused by such processes as hair color, permanent waving, bleaching, or undo stretching were eliminated.

The knotted hair was then wetted with de-ionized water by soaking the hair fibers for at least thirty minutes prior to use. Following this wetting procedure, the hair fibers were wrapped about a 7mm diameter glass rod with a uniform and consistent pressure. Six rods with the hair wrapped thereon were completely immersed in 20 mL of the desired waving solution to be tested and maintained at 30° C. for a predetermined time. In these experiments, ten minutes was employed as the application time.

When the application time was completed, the rods with the hair wrapped thereon were removed and rinsed with running water for thirty seconds. Following this rinsing step, the wrapped hair was treated for five minutes with a neutralizer composed of 2.3% $H_2O_2$ maintained at a pH of 4, by using a mixture of phosphoric acid and monobasic sodium phosphate. The neutralizer composition was maintained at temperature of 30° C. and the ratio of the neutralizer to the rods was 20 mL for every six rods.

Once this treatment time was completed, the rods with the hair wrapped thereon were removed from the neutralizer and rinsed for thirty seconds with running tap water. Then, the hair fibers were carefully removed from the glass rods and dropped onto glass plate. Each test sample was then measured to determine the hair coil diameter ($d_w$) and the hair coil length ($l_w$)

Unless otherwise specifically stated, this test procedure was employed in a plurality of additional experimental examples in order to show the unique attributes of the present invention. In conducting tests in each area of investigation, numerous samples were employed for each formulation being evaluated. In order to best present the results in a clear and understandable manner, the results obtained for $d_w$ $l_w$ are presented as the resulting average, with the overall range presented as a plus/minus value of the average.

In one area of investigation, a comparative analysis was made of various permanent waving lotions which were changed by incorporating different alpha, beta-unsaturated ketones defined by structure A. In addition, permanent waving lotions with identical constituents, except for having no alpha, beta-unsaturated ketones, were tested as control formulations.

In Table II, the values attained for $d_w$ and $l_w$ are provided for the control formulations and the formulations made in accordance with the present invention. In comparing the results attained, it is important to note that the smaller values represent tighter curls, which is indicative of a stronger waving effect.

ing tighter curls. In addition, regardless of which chemical compound was employed for providing the alpha, beta-unsaturated ketone, substantially identical enhancements were realized.

Another important discovery that was realized in developing the present invention was the fact that the amount of thioglycolate ester necessary to effect a permanent wave to a head of hair can be substantially reduced when an alpha, beta-unsaturated ketone is employed in the formulation. In Table III, experimental data is summarized which clearly shows that the overall concentration of the mercaptan is able to be reduced from 15% to 12%, with no loss of efficacy in the resulting curl in the permanently waved hair. It should be noted that the test results found in Table III for the 15% GMTG are duplicative of the test results found in Table II. In addition, all of the data contained in the following Tables has been obtained using the compositions detailed above in the foregoing Examples.

TABLE III

| WAVING LOTION | | | | WAVE EFFECT - TTTC | |
|---|---|---|---|---|---|
| Mercaptan | Additives | Conc. (%) | pH | dw (mm) | lw (mm) |
| GMTG 15% | None | — | 7.49 | 14.6 ± 0.7 | 30.2 ± 1.5 |
| GMTG 15% | Oxidized CAT | 0.025 | 7.49 | 13.3 ± 0.7 | 26.2 ± 1.5 |
| GMTG 15% | Oxidized DOPA | 0.025 | 7.49 | 12.8 ± 0.5 | 22.7 ± 1.2 |
| GMTG 15% | Oxidized DI | 0.025 | 7.49 | 12.6 ± 0.4 | 21.9 ± 1.6 |
| GMTG 15% | Oxidized CYSHQ | 0.025 | 7.50 | 12.5 ± 0.6 | 22.2 ± 1.3 |
| GMTG 15% | Oxidized PhenOH | 0.025 | 7.49 | 13.3 ± 0.6 | 24.2 ± 1.3 |
| GMTG 15% | HEM | 0.025 | 7.51 | 13.1 ± 0.5 | 24.9 ± 1.8 |
| GMTG 15% | Yel-8 | 0.025 | 7.50 | 13.4 ± 0.4 | 24.2 ± 0.7 |
| GMTG 12% (0.90N) | None | — | 8.05 | 17.8 ± 1.0 | 35.4 ± 2.0 |
| | Oxidized DOPA | 0.025 | 8.02 | 14.7 ± 0.5 | 28.1 ± 1.9 |
| | Oxidized DI Oxidized PhenOH | 0.025 | 8.01 | 14.8 ± 1.2 | 26.4 ± 0.8 |
| | DI Oxidized PhenOH | 0.025 | 8.05 | 14.5 ± 0.8 | 26.9 ± 1.3 |

TABLE II

| Permanent Wave Lotion Ingredients (% by Weight) | EXAMPLES | | | | | | | | |
|---|---|---|---|---|---|---|---|---|---|
| | 7 (Control 1) | 8 (Control 2) | 9 | 10 | 11 | 12 | 13 | 14 | 15 |
| GMTG (80%) | 18.75 | | | | | | | | |
| NH4CL | 3.00 | | | | | | | | |
| Urea | 6.00 | | | | | | | | |
| Phenoxyethanol | 1.00 | | | | | | | | |
| Ammonia (28%) | 2.50 | | | | | | | | |
| Salon Control | | 5.00* | | | | | | | |
| CAT | | | 5.00** | | | | | | |
| DL-DOPA | | | | 5.00** | | | | | |
| DAI | | | | | 5.00** | | | | |
| CysHQ | | | | | | 5.00** | | | |
| PhenOH | | | | | | | 5.00** | | |
| Hematin Soln. | | | | | | | | 5.00*** | |
| Yellow No. 8 Soln. | | | | | | | | | 5.00*** |
| D.I. Water | | | | | to 100.00 | | | | |
| pH (Adjusted) | 7.49 | 7.50 | 7.49 | 7.49 | 7.49 | 7.50 | 7.49 | 7.51 | 7.50 |
| TTTC  dw (mm) | 14.6 | 14.7 | 13.3 | 12.8 | 12.6 | 14.0 | 13.3 | 13.1 | 13.4 |
| ± | 0.7 | 0.7 | 0.7 | 0.5 | 0.4 | 0.6 | 0.6 | 0.5 | 0.4 |
| lw (mm) | 30.2 | 30.4 | 26.2 | 22.7 | 21.9 | 27.2 | 24.2 | 24.9 | 24.2 |
| ± | 1.5 | 1.8 | 3.5 | 1.2 | 1.6 | 1.8 | 2.1 | 1.8 | 0.7 |

*No Precursor, NaOH 0.25% soln.
**Precursor 0.50%, NaOH 0.25% soln., prior preparing waving lotion, oxidized by airing 1 hour
***Hematin and Yellow No. 8 0.50% were dissolved in NaOH 0.25% soln. Each precursor and color is contained 0.025% in waving lotion.

As is apparent from these results, the permanent waving lotions which incorporate alpha, beta-unsaturated ketones, in accordance with this invention, consistently and uniformly produced permanently waved hair hav- TABLE III-continued

| WAVING LOTION | | | | | |
|---|---|---|---|---|---|
| | | Conc. | | WAVE EFFECT - TTTC | |
| Mercaptan | Additives | (%) | pH | dw (mm) | lw (mm) |
| | HEM | 0.025 | 8.01 | 15.0 ± 0.8 | 27.2 ± 1.9 |

It has also been found that by increasing the amount of alpha, beta-unsaturated ketone incorporated into the permanent wave solution, an increasing benefit is realized in the resulting permanent wave. This attribute is clearly shown in Table IV where the effect of adding increasing amounts of the alpha,beta-unsaturated ketone to the wave lotion is summarized, along with the improved curled hair results.

TABLE IV

| MERCAP-TAN | ADDITIVES | | | WAVE EFFECT - TTTC | |
|---|---|---|---|---|---|
| | Structure | Conc | pH | $d_w$ | $l_w$ |
| GMTG 15% | Oxidized PhenOH | 0 | 7.50 | 12.5 ± 0.4 | 27.7 ± 1.5 |
| | | 0.001 | 7.50 | 11.5 ± 0.4 | 21.7 ± 1.3 |
| | | 0.005 | 7.50 | 11.5 ± 0.4 | 19.7 ± 1.2 |
| | | 0.010 | 7.50 | 11.2 ± 0.5 | 21.2 ± 0.8 |
| | | 0.025 | 7.51 | 11.1 ± 0.2 | 21.2 ± 1.6 |
| | | 0.050 | 7.54 | 11.5 ± 0.4 | 20.0 ± 0.9 |
| GMTG 15% | Yel-8 | 0 | 7.83 | 10.3 ± 0.2 | 26.5 ± 1.3 |
| | | 0.0001 | 7.83 | 9.7 ± 0.4 | 23.4 ± 1.0 |
| | | 0.0012 | 7.83 | 9.7 ± 0.4 | 23.8 ± 1.3 |
| | | 0.0062 | 7.83 | 9.8 ± 0.5 | 22.9 ± 1.2 |
| | | 0.0123 | 7.82 | 10.0 ± 0.2 | 22.4 ± 1.9 |
| | | 0.0615 | 7.82 | 10.1 ± 0.1 | 22.4 ± 1.3 |
| | | 0.1231 | 7.82 | 9.8 ± 0.3 | 21.6 ± 0.7 |
| GMTG 15% | Oxidized CysHQ | 0 | 7.50 | 12.7 ± 0.4 | 29.5 ± 1.8 |
| | | 0.005 | 7.50 | 11.0 ± 0.3 | 20.8 ± 0.8 |
| | | 0.025 | 7.50 | 11.4 ± 0.5 | 21.7 ± 1.3 |
| | | 0.050 | 7.50 | 11.3 ± 0.5 | 21.3 ± 1.5 |

There are several pigments within the mammalian kingdom which are highly colored and have been documented to possess important biological action, albeit without any clearly defined mode of action. For example, the class of pigments known as melanins, which are responsible for a vast majority of pigmentary action in humans, have been demonstrated to be a polymeric condensation of hydroxyindoles and/or hydroxyphenothiazine formed under oxidative conditions.

Although there is some disagreement as to whether or not the polymeric pigments have a regimented form, there is a general agreement that these pigments do contain, to some varying degree, functional sections comprised mainly of alpha,beta-unsaturated ketone. To this end, it has been found that one melanin material, specifically that attained from the ink sac of the cephalopod, sepia officianalis, was found to follow the same behavior of the synthetic materials.

While it is even more uncertain as to the true physical-chemical structure of the red mammalian pigment, pheomelanin, it has been demonstrated to be the phenothiazine polymeric condensate of L-DOPA. The material defined in Table I as PhenOH is similar in its basic components to the natural material, and the present invention mimics its structure by extensive oxidation of the synthetic precursor. In fact, this process generates a moderately water soluble reddish-brown pigment having a color similar to natural pheomelanin.

In order to further prove the efficacy of the present invention, and the substantial improvement realized by oxidizing the phenolic form into an active alpha,beta-unsaturated ketone, most of the chemicals detailed in Table I were oxidized to a black or highly colored form. The improved curl formation obtained by the use of the resulting solution in a permanent wave lotion is detailed in Table V. Included in this data is the use of melanin from sepia officianalis.

TABLE V

| | ADDITION FORM | WAVE EFFECT - TTTC | |
|---|---|---|---|
| PRECURSORS | IN WAVING LOTION[1] | $d_w$ (mm) | $l_w$ (mm) |
| — | None (Control) | 14.6 ± 0.7 | 30.2 ± 1.5 |
| Hydroquinone | Oxidized, 0.025% | 12.0 ± 0.5 | 24.3 ± 1.6 |
| Catechol | Oxidized, 0.025% | 13.3 ± 0.7 | 26.2 ± 1.5 |
| 3,4-Dihydroxy phenylalanine | Oxidized, 0.025% | 12.8 ± 0.5 | 22.7 ± 1.2 |
| 5-Hydroxyindole | Oxidized, 0.025% | 12.0 ± 0.2 | 22.2 ± 0.9 |
| 5,6-Dihydroxyindole | Oxidized, 0.025% | 12.6 ± 0.4 | 21.9 ± 1.6 |
| N-Methyl-5,6,Dihydroxindole | Oxidized, 0.025% | 12.2 ± 0.4 | 23.1 ± 1.2 |
| 2-S-Cysteinyl-1,4-hydroquinone | Oxidized, 0.025% | 12.5 ± 0.6 | 22.2 ± 1.3 |
| 3'-Hydroxy-2,2,3,3,-tetrahydro phenothiazine | Oxidized, 0.025% | 13.3 ± 0.6 | 24.2 ± 1.3 |
| COLORS | | | |
| Hematin | 0.025% | 13.1 ± 0.5 | 24.9 ± 1.8 |
| Lawsone | 0.025% | 12.5 ± 0.5 | 23.2 ± 0.6 |
| D&C Yellow No. 8 | 0.025% | 13.4 ± 0.4 | 24.2 ± 0.7 |
| NATURAL MELANIN | | | |
| Melanin (Sepia officianalis) | Alkalitreated 0.025% | 12.0 ± 0.3 | 21.3 ± 1.3 |

[1]Waving Lotion: GMTG 15%, NH₄CL 3.0%, Urea 6.0%, Phenoxyethanol 1.0%, Ammonia Water & Deionized Water qs 100.0%, pH = 7.50 ± 0.01

The final principal benefit which is obtained by incorporating alpha,beta-unsaturated ketone in permanent waving lotions, as detailed above, is the dramatic reduction that results in the residual malodor associated with permanent waving, as effected by mercaptans. While the origin of this residual malodor is unknown, the gas of molecular formula, $H_2S$, (hydrogen sulfide) closely resembles this odor. By employing the present invention, it has been found that the relative amount of malodor decreases with decreasing content of $H_2S$, which has been found to decrease in direct proportional relationship to the increased amount of alpha,beta-unsaturated ketone employed.

In a typical test, 1 gram of virgin human hair was permanently waved using a composition as described in Examples 1 through 6. Next, an alpha,beta-unsaturated ketone created from the precursor chemicals or chemicals detailed in Table I was added to an Erlenmeyer flask containing 20 mL of phosphate buffer at pH 7 and 8% to 12% GMTG. The mixture was incubated at 40° C. for five hours and the headspace gases evaluated for hydrogen sulfide formation as determined with a commercially available sensor tube, obtained from Matheson Gas Company.

In Table VI, the test results obtained are shown, detailing the values for hydrogen sulfide (H2S) evolution under these conditions. In addition to using the materials detailed in Table I, tests were also conducted without using the inclusion of any alpha, beta-unsaturated ketone, as a control.

TABLE VI

| Test Additive | Con. % | pH | Detection of Hydrogen Sulfide in ppm per Volume of Gases Examined | | |
|---|---|---|---|---|---|
| | | | 100 ml | 200 ml | 300 ml |
| None | — | 6.95 | 360 | 650 | 850 |
| | — | 7.36 | 380 | 660 | 900 |
| | — | 7.40 | 370 | 640 | 870 |
| | — | 7.53 | 385 | 650 | 850 |
| (Average Value) | | | 374 ± 11 | 650 ± 8 | 868 ± 24 |
| Yellow No. 8 | 0.125 | 6.99 | 267 | 465 | 572 |
| | 0.125 | 7.42 | 284 | 445 | 543 |
| (Average Value) | | | 276 | 455 | 558 |
| Oxidized CAT | 0.125 | 6.93 | 116 | 175 | 202 |
| Oxidized DOPA | 0.125 | 6.91 | 164 | 243 | 278 |
| Oxidized DI | 0.125 | 6.75 | 45 | 50 | 55 |
| Oxidized CYSHQ | 0.125 | 6.89 | 57 | 65 | 73 |
| Oxidized PhenOH | 0.125 | 6.90 | 30 | 30 | 30 |
| HEMA | 0.125 | 6.93 | 0 | 4 | 4 |
| | | 7.35 | 16 | 17 | 20 |
| | | 7.35 | 0 | 5 | 10 |
| | | 7.53 | 5 | 5 | 5 |
| (Average Value) | | | 5 ± 8 | 8 ± 6 | 10 ± 7 |
| Oxidized 5-HI | 0.125 | 6.68 | 139 | 200 | 207 |
| Oxidized HQ | 0.125 | 6.75 | 76 | 104 | 125 |
| Oxidized NMDI | 0.125 | 6.54 | 51 | 71 | 76 |
| Lawsone | 0.125 | 6.80 | 360 | 622 | — |
| Melanin SEP (Alkali Treated) | 0.125 | 6.86 | 64 | 79 | 91 |

As is clearly apparent from the results detailed in Table VI, the use of alpha, beta-unsaturated ketones in permanent waving lotions, in accordance with the present invention, is able to virtually eliminate the presence of hydrogen sulfide. Although some of the alpha, beta-unsaturated ketones are not as effective, most of the compositions tested were able to reduce the hydrogen sulfide by between about 60% to 100%.

It will thus be seen that the objects set forth above, among those made apparent from the preceding description, are efficiently attained and, since certain changes may be made in carrying out the compositions detailed herein as well as in carrying out the above method without departing from the scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Particularly, it is to be understood that in said claims, ingredients or compounds recited in the singular are intended to include compatible mixtures of such ingredients wherever the sense permits.

Having described our invention, what we claim as new and desire to secure by Letters Patent is:

1. A method for permanently waving a head of hair comprising the steps of
   A. preparing an aqueous solution consisting essentially of
      a. an organic compound
         1. capable of reacting with alkaline material or being oxidized to form an alpha, beta-unsaturated ketone comprising the following structure

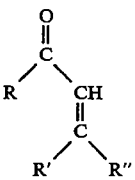

wherein R, R', R"=H, CH3, CH2—, aryl, cyclic aliphatics, and/or members of cyclic aliphatics, and
         2. selected from the group consisting of Catechol, 3,4 Dihydroxyphenylalanine, 4-Hydroxyindole, 5-Hydroxyindole, 2-S-Cysteinyl-1,4-hydroquinone, 3'-Hydroxy-2,2,3,3-tetrahydrophenothiazine, Hematoxylin, Hydroquinone, 5,6-Dihydroxyindole, and N-Methyl-5,6-dihydroxyindole, and
      b. a member selected from the group consisting of oxidizing agents and alkali materials;
   B. intermixing the components of the aqueous solution for a sufficient amount of time to enable substantially all of the organic compound to be activated into the alpha, beta-unsaturated ketone;
   C. mixing the aqueous solution into a permanent waving lotion consisting essentially of a hydroxylated ester of an organic acid of sulfur in sufficient quantity to obtain a permanent waving lotion having between about 0.001% and 0.1% by weight of the activated alpha, beta-unsaturated ketone and between about 7% and 20% by weight of the hydroxylated ester of an organic acid of sulfur,
   D. applying the permanent waving lotion to a head of hair and allowing the lotion to remain on the hair for the desired processing time;
   E. removing the permanent waving lotion from the hair; and
   F. applying a neutralizing or oxidizing composition to the hair.

2. The method defined in claim 1, and comprising the additional step of:
   G. intermixing as part of the permanent waving lotion the following ingredients:
      a. between about 1% and 20% by weight of one or more members selected from the group consisting of ammonium chloride, ammonium sulfonate, ammonium citrate, guanidine carbonate, urea, dimethyl urea, hydrolyzed silk protein, hydrolyzed soy protein, cocobetaine, L-arginine, phenoxyethanol, Laureth -23, Laureth -25, fragrances, Oleth -20, Oleth -23, and preservatives; and
      b. deionized water forming the balance.

3. The method defined in claim 2, comprising the additional step of

H. intermixing in the permanent wave lotion an alkalizing agent in a sufficient quantity to maintain the pH of the permanent waving lotion at between about 7 and 8.5.

4. A permanent waving lotion for use with a neutralizer for imparting a curl formation to the hair while also substantially reducing the malodor typically associated with permanently waved hair, said permanent waving lotion consisting essentially of
   A. between about 7% and 20% by weight of a hydroxylated ester of an organic acid of sulfur,
   B. between about 0.001% and 0.1% by weight of an organic compound having at least one functional position definable as an alpha, beta-unsaturated ketone in conjunction with a carbon-carbon double bond and comprising the following structure:

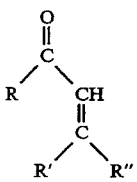

wherein R, R', R"=H, CH₃, CH₂—, aryl, cyclic aliphatics, and/or members of cyclic aliphatics,
   C. between about 1% and 20% by weight of one or more members selected from the group consisting of ammonium chloride, ammonium sulfonate, ammonium citrate, guanidine carbonate, urea, dimethyl urea, hydrolyzed silk protein, hydrolyzed soy protein, cocobetaine, L-arginine, phenoxyethanol, Laureth -23, Laureth-25, fragrances, Oleth -20, Oleth -23, and preservatives;
   D. an alkalizing agent in sufficient quantity to maintain the pH of the permanent waving lotion at between about 7 and 8.5; and
   E. deionized water forming the balance.

5. The permanent waving lotion defined in claim 4, wherein said lotion is further defined as comprising a first part and a second part, both of which are intermixed immediately before application to the hair, and the first part is further defined as comprising an alkaline solution incorporating the alpha, beta-unsaturated ketone and the alkalizing agent in sufficient quantity to keep the pH of the solution at about 9 and the second part is further defined as comprising an aqueous solution incorporating between about 11% and 25% by weight of the hydroxylated ester of an organic acid of sulfur.

6. The permanent waving lotion defined in claim 4, wherein the alpha, beta-unsaturated ketone is further defined as being formed from a precursor selected from the group consisting of Catechol, 3,4 Dihydroxyphenylalanine, 4-Hydroxyindole, 5-Hydroxyindole, 2-S-Cysteinyl-1,4-hydroquinone, 3'-Hydroxy-2,2,3,3-tetrahydrophenothiazine, Hematoxylin, Hydroquinone, 5,6-Dihydroxyindole, and N-Methyl-5,6-dihydroxyindole.

7. The permanent waving lotion defined in claim 6, wherein said alpha, beta-unsaturated ketone is further defined as being formed by intermixing the precursor in an aqueous solution with a member selected from the group consisting of oxidizing agents and alkali materials.

8. The permanent waving lotion defined in claim 4, wherein said hydroxylated ester of an organic acid sulphur is further defined as comprising an ester of thioglycolic acid which comprises a functional group selected from the group consisting of an aliphatic, hydroxy aliphatic, aryl and alkoxy amines.

9. The permanent waving lotion defined in claim 9, wherein the alpha, beta-unsaturated ketone is further defined as comprising one selected from the group consisting of hematin, lawsone, D & C Yellow No. 8 and melanin.

10. The permanent waving lotion defined in claim 9, wherein the alpha, beta-unsaturated ketone is further defined as being formed, prior to intermixing with the other components of the permanent wave lotion, from an aqueous solution comprising
   a. a precursor selected from the group consisting of Catechol, 3,4 Dihydroxyphenylalanine, 4-Hydroxyindole, 5-Hydroxyindole, 2-S-Cysteinyl-1,4-hydroquinone, 3'-Hydroxy-2,2,3,3-tetrahydrophenothiazine, Hematoxylin, Hydroquinone, 5,6-Dihydroxyindole, and N-Methyl-5,6-dihydroxyindole, and
   b. an ingredient forming the desired alpha, beta-unsaturated ketone from the precursor, with said ingredient being selected from the group consisting of oxidizing agents and alkali materials.

* * * * *